United States Patent [19]

Arano et al.

[11] Patent Number: 4,559,221

[45] Date of Patent: Dec. 17, 1985

[54] P-GLYOXYLOYLPHENYLALKANOIC ACID BIS(THIOSEMICARBAZONE) DERIVATIVES, AND THEIR PRODUCTION AND USE

[75] Inventors: Yasushi Arano, Uji; Yasuhiro Magata, Kyoto; Akira Yokoyama, Otsu, all of Japan

[73] Assignee: Nihon Medi-Physics Co., Ltd., Hyogo, Japan

[21] Appl. No.: 539,884

[22] Filed: Oct. 7, 1983

[30] Foreign Application Priority Data

Apr. 19, 1983 [JP] Japan ................................. 58-68850
Apr. 19, 1983 [JP] Japan ................................. 58-68851

[51] Int. Cl.⁴ ...................... A61K 49/00; A61K 43/00
[52] U.S. Cl. ........................................ 424/1.1; 424/9; 564/20
[58] Field of Search ...................... 424/1.1, 9; 564/20

[56] References Cited

U.S. PATENT DOCUMENTS

| 3,382,275 | 5/1968 | Barrett ................... 564/20 |
| 3,709,935 | 1/1973 | Barrett ................... 564/20 |
| 3,824,276 | 7/1974 | Murray et al. ........... 564/20 |
| 4,287,362 | 9/1981 | Yokoyama et al. .... 424/1.1 |
| 4,338,248 | 7/1982 | Yokoyama et al. .... 424/1.1 |

FOREIGN PATENT DOCUMENTS

| 0054920 | 6/1982 | European Pat. Off. ............. 424/1.1 |
| 0074429 | 8/1983 | European Pat. Off. ............. 424/1.1 |
| 0966849 | 8/1964 | United Kingdom ................. 424/323 |
| 0356274 | 11/1972 | U.S.S.R. ............................. 564/19 |

OTHER PUBLICATIONS

Japanese Journal of Nuclear Medicine, vol. 19, No. 9, p. 1336, issued Oct. 20, 1982 (with translation).
Yokoyama et al, Chem. Abstracts, 101, (1984), #35249u.
Yokoyama et al, Chem. Abstracts, 85, (1976), #139238g.

Primary Examiner—Christine M. Nucker

[57] ABSTRACT

A radioactive diagnostic agent which comprises a physiologically active substance and a radioactive metallic element combined with a compound of the formula:

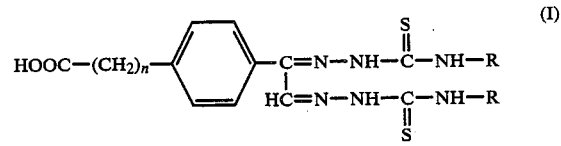

wherein R is a hydrogen atom or a $C_1$–$C_3$ alkyl group and n is an integer of 0 to 4. The agent is characteristic in having a high stability even after being administered into a human body and showing the substantially the same behavior as the physiologically active substance itself in a human body.

20 Claims, 1 Drawing Figure

P-GLYOXYLOYLPHENYLALKANOIC ACID BIS(THIOSEMICARBAZONE) DERIVATIVES, AND THEIR PRODUCTION AND USE

The present invention relates to p-glyoxyloylphenylalkanoic acid bis(thiosemicarbazone) derivatives, and their production and use. More particularly, it relates to p-glyoxyloylphenylalkanoic acid bis(thiosemicarbazone) derivatives (hereinafter referred to as "GPTS") of the formula:

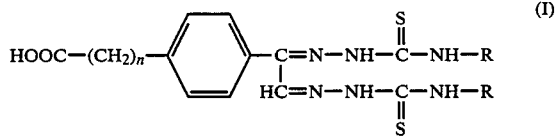

wherein R is a hydrogen atom or a $C_1-C_3$ alkyl group and n is an integer of 0 to 4, their preparation process and their use as a carrier for a radioactive metallic element as well as a physiologically active substance.

For the purpose of a non-invading nuclear medical diagnosis such as recording, dynamic study and quantitative measurement of the blood circulation system, detection of physiological abnormality or localization of abnormality by imaging, there have been widely used physiologically active substances labeled with iodine-131 ($^{131}$I) such as $^{131}$I-labeled serum albumin and $^{131}$I-labeled fibrinogen. However, $^{131}$I has a long half life of about 8 days and emits betarays so that the patient administered therewith is exposed to a large quantity of radiation.

In order to overcome the said drawback in the $^{131}$I-labeled physiologically active substances, attempts have been made to provide radioactive diagnostic agents comprising physiologically active substances and radioactive metallic elements having more favorable physical properties than iodine-131 combined thereto. Among such attempts, there is known a labeling method wherein a physiologically active substance is treated directly with a radioactive metal salt to make a chelate compound, which may be used as a radioactive diagnostic agent. For instance, human serum albumin is treated with an aqueous solution containing technetium-99m ($^{99m}$Tc) in the form of pertechnetate in the presence of a reducing agent to give $^{99m}$Tc-labeled human serum albumin. Further, for instance, bleomycin is treated with an aqueous solution containing indium-111 ($^{111}$In) in the form of indium chloride to give $^{111}$In-labeled bleomycin. However, the chelate forming property of those physiologically active substances is not sufficient, and the once formed chelating bond is readily broken. In fact, $^{99m}$Tc-labeled serum albumin and $^{111}$In-labeled bleomycin are low in the stability after administration into living bodies so that the behavior of the radioactivity in such bodies does not coincide with that of serum albumin or bleomycin as the physiologically active substance. This is a fatal defect for the nuclear medical diagnosis based on the exact trace of the behavior of the radioactivity which should coincide with the behavior of the physiologically active substance.

As a result of the extensive study, it has now been found that the GPTS (I) has a strong chelate-forming property and can be bonded to an amino group inherently present or artificially introduced in physiologically active substances under a mild condition. It has also been found that a chemical product comprising a physiologically active substance and a radioactive metallic element bonded thereto with intervention of the GPTS (I) is sufficiently stable in living bodies, and the behavior of the radioactivity in living bodies is quite coincident with that of the physiologically active substance itself.

As the chelating agent for preparation of a radioactive diagnostic agent, there are known 2-oxopropionaldehyde bis(thiosemicarbazone) derivatives (U.S. Pat. No. 4,287,362). In comparison with such known chelating agents, the GPTS is favorable in showing a less interaction onto the physiologically active substance combined therewith. Further, the GPTS can be produced more easily than the known chelating agents.

DETAILED DESCRIPTION

Figure 1:
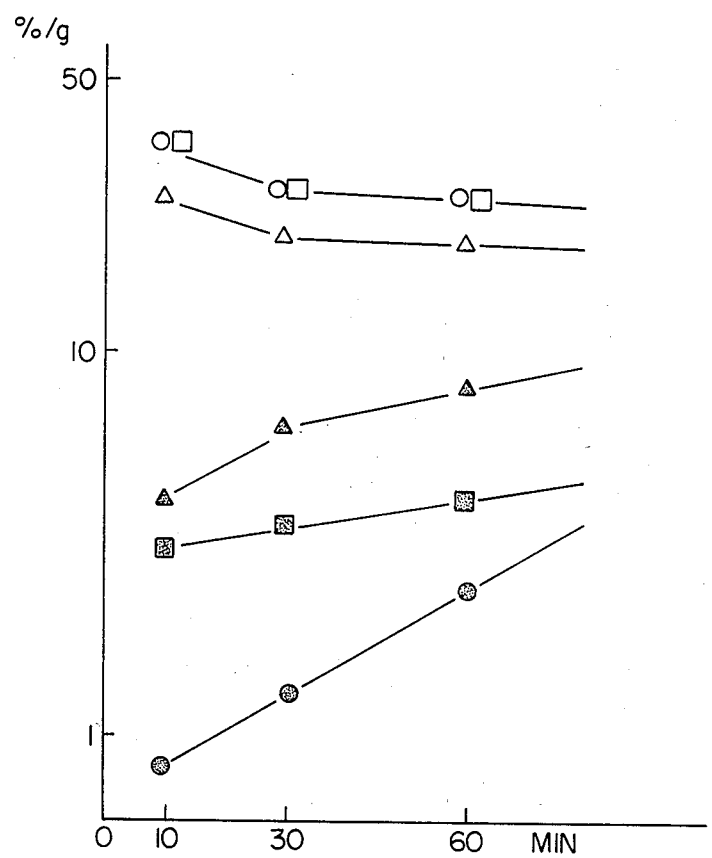
FIG. 1 is a graph of results in Example 11 depicting variation of blood level and radioactivity concentration in the stomach with time comparing a diagnostic agent of the invention with commercial products.

According to the present invention, there is provided the GPTS (I), which is useful as a chemical carrier for a physiologically active substance and a radioactive metallic element. There is also provided the physiologically active substance-combined GPTS (I) comprising the GPTS (I) and a physiologically active substance chemically bonded thereto with or without intervention of any linking aid, which is useful as a non-radioactive carrier to be used in diagnosis in nuclear medicine. There is further provided the radioactive metallic element-labeled, physiologically active substance-combined GPTS (I) comprising the physiologically active substance-combined GPTS (I) and a radioactive metallic element chelated thereto, which is useful as a radioactive diagnostic agent.

The GPTS (I) is novel and can be produced according to the following reaction scheme:

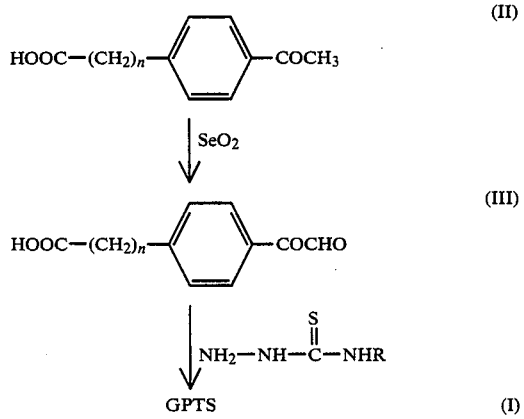

wherein R and n are each as defined above.

The p-acetylphenylalkanoic acid (II) is oxidized with selenium dioxide to the p-glyoxyloylphenylalkanoic acid (III), which is then condensed with thiosemicarbazide or its N-alkyl derivative to give the GPTS (I). The oxidation with selenium dioxide is usually carried out in an inert solvent (e.g. tetrahydrofuran, dioxane, ether) while refluxing. The subsequent condensation with thiosemicarbazide or its N-alkyl derivative is normally carried out in the presence of an acidic catalyst (e.g. hydrochloric acid, hydrobromic acid, sulfuric acid) in an inert solvent (e.g. methanol, ethanol). The intermediarily produced p-glyoxyloylphenylalkanoic acid (III) is not necessarily required to be isolated from the reaction mixture. In other words, the reaction mixture obtained in the oxidation step and comprising the p-glyoxyloylphenylalkanoic acid (III) may be as such employed for the reaction in the condensation step.

The GPTS (I) thus produced has two thiosemicarbazone groups which can catch a radioactive meallic element to form a chelate and a carboxyl group which can be bonded to an amino group inherently present or artificially introduced in a physiologically active substance with or without intervention of any linking aid under a mild condition to fix such physiologically active substance firmly. Therefore, it is useful as a carrier for the radioactive metallic element and the physiologically active substance.

For manufacture of the radioactive diagnostic agent of the present invention, the GPTS (I) is usually first combined with a physiologically active substance, and then the resultant combined product is labeled with a radioactive metallic element.

The term "physiologically active substance" is intended to mean any substance which can show a specific accumulability at a certain organ or tissue or a certain diseased locus or exhibits a specific behavior corresponding to a certain physiological state. Tracing of its behavior in a living body can provide informations useful for diagnosis. Such physiologically active substance as having an amino group is usable advantageously in this invention. Even when an amino group is not present, it may be used by introducing previously an amino group (or an amino-bearing group) therein. Specific examples of the physiologically active substance are blood proteins (e.g. human serum albumin, fibrinogen), enzymes (e.g. urokinase, streptokinase), hormones (e.g. thyroid stimulating hormone, parathyroid hormones), immune antibodies (e.g. IgG), antibiotics (e.g. bleomycin, kanamycin), saccharides, fatty acids, amino acids, etc.

The combination of the GPTS (I) with a physiologically active substance may be carried out according to any procedure as conventionally adopted for linking a carboxyl group with an amino group to make a carbonamide linkage (—CONH—). Examples of such procedure include the carbodiimide process, the azide process, the mixed acid anhydride process, the acid chloride process, etc. According to the carbodiimide process, the GPTS (I) having a carboxyl group and a physiologically active substance having an amino group are condensed in the presence of a carbodiimide such as 1-cyclohexyl-3-(2-morpholinyl-4-ethyl)carbodiimide or 1-ethyl-3-(3-dimethylaminopropyl)carbodiimide to form a carbonamide linkage between the carboxyl group and the amino group. According to the azide process, the GPTS (I) having a carboxyl group is previously converted into an azide by treatment with an azidating agent (e.g. hydrazine, diphenylphosphoroazidate) and then reacted with a physiologically active substance having an amino group to form a carbonamide linkage. These bonding procedures are quite advantageous in accomplishment of the bonding under a mild condition so that any inactivation, denaturation or decomposition of the physiologically active substance does not materially take place.

When desired, the thus prepared physiologically active substance-combined (hereinafter referred to as "PAS-combined") GPTS (I) may be purified by a per se conventional procedure such as dialysis, gel filtration or column chromatography so as to eliminate impurities such as unreacted reagents therefrom. As the result, the combined product is usually obtained in the form of an aqueous solution, and this aqueous solution may be as such used for labeling with a radioactive metallic element. Alterntively, the aqueous solution may be subjected to lyophilization, evaporation under reduced pressure at low temperatures or the like to obtain a dried product, which also can be used as such or in the form of solution for labeling. Depending upon the use, the said aqueous solution or the said dried product may be incorporated with any additive such as a pH controlling agent (e.g. an acid, a base, a buffer), a stabilizer (e.g. ascorbic acid), an isotonizing agent (e.g. sodium chloride) or a preserving agent (e.g. benzyl alcohol). In addition, the said aqueous solution or the said dried product may contain any reducing or oxidizing agent, which will act on a radioactive metallic element to be labeled so as to give a stable chelate product, as hereinafer explained. Still, the PAS-combined GPTS (I) is per se quie stable and can be readily labeled with a radioactive metallic element by a simple procedure as hereinafter explained, and therefore it may be stored and supplied on the demand so that the work for its production from the GPTS (I) and the physiologically active substance by the practitioner such as a medical doctor can be saved.

For the labeling of the PAS-combined GPTS (I) as the non-radioactive carrier with a radioactive metallic element, the PAS-combined GPTS (I) may be treated with the radioactive metallic element in an appropriate form.

The term "radioactive metallic element" is intended to mean any metallic element having radioactivity, which has physical characteristics suitable for nuclear medical diagnosis. Specific examples of the radioactive metallic element are gallium-67 ($^{67}Ga$), gallium-68 ($^{68}Ga$), thallium-201 ($^{201}Tl$), $^{111}In$, $^{99m}Tc$, etc. They are normally employed in their salt forms, particularly in their water-soluble salt forms.

Depending upon the kind or state of the radioactive metallic element, there may be adopted two different labeling manners. When the radioactive metallic element is in a valency state which is not required to be reduced or oxidized for formation of a stable chelate compound, the PAS-combined GPTS (I) is contacted with the radioactive metallic element in an aqueous medium to obtain the radioactive metallic element-labeled, PAS-combined GPTS (I). This labeling manner may be applied to $^{67}Ga$, $^{111}In$, etc. When the radioactive metallic element is in a valency state which is required to be reduced or oxidized for formation of a stable chelate compound, the PAS-combined GPTS (I) is contacted with the radioactive metallic element in an aqueous medium in the presence of a reducing agent or an oxidizing agent to obtain the radioactive metallic element-labeled, PAS-combined GPTS (I). This labeling manner may be applied to $^{99m}Tc$, etc.

As the reducing agent, there may be usually employed a stannous salt, i.e. a salt of divalent tin ion ($Sn^{++}$). Specific examples are stannous halides (e.g. stannous chloride, stannous fluoride), stannous sulfate, stannous nitrate, stannous acetate, stannous citrate, etc.

Sn++ ion-bearing resins such as ion-exchange resins charged with Sn++ ion are also usable.

When, for instance, the radioactive metallic element is $^{99m}$Tc, the PAS-combined GPTS (I) may be treated in the presence of a reducing agent such as a stannous salt. As to the order of the introduction of the above reagents into the reaction system, any particular limitation does not exist. Usually, however, the mixing of the stannous salt with the pertechnetate in an aqueous medium in the first place should be avoided. The stannous salt may be used in such an amount as can reduce sufficiently the pertechnetate.

The radioactive diagnostic agent should have sufficient radioactivity and radioactivity concentration which can assure reliable diagnosis. For instance, in case of the radioactive metallic element being $^{99m}$Tc, it may be included usually in an amount of 0.1 to 50 mCi in about 0.5 to 5.0 ml at the time of administration. The amount of the PAS-combined GPTS (I) may be such as sufficient to form a stable chelate compound with the radioactive metallic element.

The thus produced radioactive metallic element-labeled, PAS-combined GPTS (I) as the radioactive diagnostic agent is sufficiently stable, and therefore it may be stored as such and supplied on the demand. When desired, the radioactive diagnostic agent may contain any additive such as a pH controlling agent (e.g. an acid, a base, a buffer), a stabilizer (e.g. ascorbic acid) or an isotonizing agent (e.g. sodium chloride).

The radioactive metallic element-labeled, PAS-combined GPTS (I) of this invention is useful for nuclear medical diagnosis. For instance, $^{99m}$Tc-labeled, human serum albumin-combined GPTS (I) can be used for recording, dynamic study and quantitative measurement of the blood circulation system by administering intravenously to a human body. Further, for instance, $^{99m}$Tc-labeled, fibrinogen-combined GPTS (I) or $^{99m}$Tc-labeled, urokinase-combined GPTS (I) may be used for detection and recording of thrombosis as well as localization of thrombosis, since they accumulate at the locus of thrombosis. Further, for instance, $^{99m}$Tc-labeled, streptokinase-combined GPTS (I) is useful for determination of the locus of myocardial infarction. Moreover, for instance, $^{99m}$Tc-labeled, thyroid stimulating hormone-combined GPTS (I) is useful for detection and recording of a cancer at the thyroid gland.

The radioactive diagnostic agent of this invention may be administered to patients in an amount sufficient to produce a radioactivity necessary for examination of the organ or tissue by an appropriate route, usually through an intravenous route. For instance, the intravenous administration of a $^{99m}$Tc-labeled radioactive diagnostic agent of about 1 to 3 ml in volume having a radioactivity of about 1 to 20 mCi to a patient is quite suitable for the diagnostic purpose.

The advantages of the PAS-combined GPTS (I) as a non-radioactive carrier may be summarized as follows: (a) it is stable over a long period of time after manufacture; (b) since it can be produced under a mild condition, any unfavorable side reaction such as inactivation, denaturation or decomposition is not materially caused to the physiologically active substance; (c) any physiologically active substance having an amino group is usable as the starting material; (d) even when an amino group is not present, the introduction of such group into a physiologically active substance makes it usable as the starting material; (e) by such a simple procedure as contacting with a radioactive metallic element in an aqueous medium, it can afford a radioactive metallic element-labeled, PAS-combined GPTS (I); (f) the PAS-combined GPTS can retain the physiological activity inherent in the physiologically active substance therein without any material influence by the GPTS (I) therein. Likewise, the advantages of the radioactive metallic element-labeled, PAS-combined GPTS (I) as a radioactive diagnostic agent may be summarized as follows: (a) it is stable over a long period of time after manufacture; (b) the labeling efficiency with the radioactive metallic element is extremely high (nearly 100%); (c) since the labeling operation is quite simple, any unfavorable side reaction such as inactivation, denaturation or decomposition is not caused to the physiologically active substance bonded to the GPTS (I); (d) among various radioactive metallic elements, the most suitable one for the diagnostic purpose may be chosen and used so that the informations for diagnosis is enhanced not only in quantity but also in quality with reduction of the exposure dose.

Practical and presently preferred embodiments of the invention are illustratively shown in the following Examples wherein % is by weight, unless otherwise defined.

EXAMPLE 1

Production of p-glyoxyloylphenylacetic acid bis(N-methylthiosemicarbazone) (hereinafter referred to as "GPAMTS"):

To a solution of p-acetylphenylacetic acid (1.78 g) in dioxane (30 ml), selenium dioxide (1.22 g) was added, and the resultant mixture was refluxed for 7 hours. After removal of the dioxane by distillation, the residue was dissolved in ethanol (25 ml), treated with activated carbon and filtered to eliminate the selenium dioxide. The filtrate was dropwise added to N hydrochloric acid (15 ml) containing N-methylthiosemicarbazide (2.1 g) heated at 60° C. The precipitated crystals were collected by filtration and recrystallized from 60% ethanol containing activated carbon to give p-glyoxyloylphenylacetic acid bis(N-methylthiosemicarbazone) (GPAMTS) (1.10 g). M.P., 223° to 224° C. Rf=0.34 (silica gel; chloroform:acetone:acetic acid=90:10:1).

EXAMPLE 2

Production of p-glyoxyloylphenylpropionic acid bis(N-methylthiosemicarbazone) (hereinafter referred to as "GPPMTS"):

To a solution of p-acetylphenylpropionic acid (1.92 g) in dioxane (30 ml), selenium dioxide (1.22 g) was added, and the resultant mixture was refluxed for 6 hours. The reaction mixture was allowed to stand at room temperature overnight. After removal of the dioxane by distillation, the residue was dissolved in ethanol (20 ml), treated with activated carbon and filtered to eliminate the selenium dioxide. The filtrate was dropwise added to N hydrochloric acid (15 ml) containing N-methylthiosemicarbazide (2.1 g) heated at 60° C. The precipitated crystals were collected by filtration and recrystallized from 60% ethanol containing activated carbon to give p-glyoxyloylphenylpropionic acid bis(N-methylthiosemicarbazone) (GPPMTS) (1.14 g). M.P., 216° to 217° C. Rf=0.36 (silica gel; chloroform:acetone:acetic acid=90:10:1).

EXAMPLE 3

Production of p-glyoxyloylphenylbutyric acid bis(N-methylthiosemicarbazone)(GPBMTS):

To a solution of p-acetylphenylbutyric acid (2.06 g) in dioxane (30 ml), selenium dioxide (1.22 g) was added, and the resultant mixture was refluxed for 5 hours. After removal of the dioxane by distillation, the residue was dissolved in ethanol (20 ml), treated with activated carbon and filtered to eliminate the selenium dioxide. The filtrate was dropwise added to N hydrochloric acid (15 ml) containing N-methylthiosemicarbazide (2.31 g) heated at 60° C. The precipitated crystals were collected by filtration and recrystallized from 60% ethanol containing activated carbon to give p-glyoxyloylphenylbutyric acid bis(N-methylthiosemicarbazone) (GPBMTS) (1.20 g). M.P., 208° to 209° C. Rf=0.45 (silica gel; chloroform:acetone:acetic acid=90:10:1).

EXAMPLE 4

Production of p-glyoxyloylphenylvaleric acid bis(N-methylthiosemicarbazone) (GPVMTS):

To a solution of p-acetylphenylvaleric acid (3.3 g) in dioxane (50 ml), selenium dioxide (1.83 g) was added, and the resultant mixture was refluxed for 3 hours. After removal of the selenium dioxide by filtration, the filtrate was concentrated under reduced pressure. The residue was dissolved in methanol, treated with activated carbon and filtered. The filtrate was dropwise added to N hydrochloric acid (15 ml) containing N-methylthiosemicarbazide (2.1 g) heated at 60° C. The precipitated crystals were collected by filtration and recrystallized from 60% ethanol containing activated carbon to give p-glyoxyloylphenylvaleric acid bis(N-methylthiosemicarbazone) (GPVMTS) (1.84 g). M.P., 195° to 197° C. Rf=0.45 (silica gel; chloroform:acetone:acetic acid=90:10:1).

EXAMPLE 5

Preparation of human serum albumin-combined GPPMTS as a non-radioactive carrier:

On an ice bath, human serum albumin (lyophilized; 170 mg) was dissolved in 0.01M borate buffer (pH 9.5) (10 ml) to give the solution (A). Separately, GPPMTS (19.0 mg) was dissolved in dimethylformamide (0.5 ml) on an ice bath, and triethylamine (7 μl) and diphenylphosphoroazide (11.86 μl) were added thereto in this order. The resultant mixture was stirred on an ice bath for 1 hour to give the solution (B). On an ice bath, the entire amount of the solution (B) thus obtained is added to the solution (A), followed by stirring for 1 hour. The reaction mixture was charged in a conventional tube for dialysis and subjected to dialysis to an acetate buffer (pH 5.0) having an ion intensity of 0.025 for about 24 hours. By centrifugation (1000 rpm, 30 minutes), a solid material was precipitated. The supernatant was added to a column of DEAE cephallose (5 cm in diameter; 30 cm in height), and the column was washed with an acetate buffer (pH 5.0) having an ion intensity of 0.025. Then, an acetate buffer (pH 4.65) having an ion intensity of 0.025 was passed through the column. The eluted solution was adjusted to make a concentration of human serum albumin of 10 mg/ml. Each one ml was filled in a vial flushed with nitrogen gas and lyophilized to give a non-radioactive carrier preparation. The above operations were effected under a sterile condition.

The non-radioactive carrier prepared in this Example was white, cotton-like crystals. When dissolved in water, there was obtained a pale yellow, transparent solution.

EXAMPLE 6

Preparation of human serum albumin-combined GPPMTS as a non-radioactive carrier:

In the same manner as in Example 5 but adding stannous chloride to the solution just before charging to a vial to make a concentration of 5.7 μg/ml, there was prepared the non-radioactive carrier filled in a vial. When dissolved in water, there was obtained a pale yellow transparent solution.

EXAMPLE 7

Preparation of human serum albumin-combined GPVMTS as a non-radioactive carrier:

On an ice bath, human serum albumin (lyophilized; 170 mg) was dissolved in water (10 ml) and adjusted to pH 8.2 with a 0.1N sodium hydroxide solution to give the solution (A). Separately, GPVMTS (20.4 mg) was dissolved in dimethylformamide (0.5 ml) and cooled to a temperature of −5° to −10° C. To the resultant solution, isobutyl chloroformate (7.2 μl) and tri-n-butylamine (13.1 μl were added in order, followed by stirring for 30 minutes to give the solution (B). On an ice bath, the entire amount of the solution (B) was added to the solution (A), followed by stirring for 1 hour. The reaction mixture was purified as in Example 5 and adjusted to make a concentration of human serum albumin of 10 mg/ml. Further, stannous chloride was added thereto to make a concentration of 5.7 μg/ml. The resulting solution was charged in a vial, followed by lyophilization to give a non-radioactive carrier preparation-omposition. The above operations were carried out under a sterial condition.

When dissolved in water, there was obtained a pale yellow, transparent solution.

EXAMPLE 8

Preparation of $^{99m}$Tc-labeled, human serum albumin-combined GPPMTS as a radioactive diagnostic agent:

The human serum albumin-combined GPPMTS obtained in Example 5 was dissolved in an acetate buffer (pH 3.4) (1 ml), a cationic exchange resin (3 mg) adsorbing stannous ion (7 μg in terms of stannous chloride) thereon was added thereto. Then, a physiological saline solution (1.0 ml) containing $^{99m}$Tc (1.0 mCi) in the form of sodium pertechnetate, followed by stirring for 15 minutes. The resultant solution was allowed to stand at room temperature for more than 3 hours and passed through a membrane filter of 0.22 μm in pore size to obtain the $^{99m}$Tc-labeled, human serum albumin-combined BMTS useful as a radioactive diagnostic agent.

This solution was pale yellow, transparent and had a pH of around 3.4.

EXAMPLE 9

Preparation of $^{99m}$Tc-labeled, human serum albumin-combined GPPMTS as a radioactive diagnostic agent:

To the human serum albumin-combined GPPMTS obtained in Example 6, a physiological saline solution (1.0 ml) containing $^{99m}$Tc (1.0 mCi) in the form of sodium pertechnetate, followed by stirring for 15 minutes to obtain the $^{99m}$Tc-labeled, human serum albumin-combined GPPMTS useful as a radioactive diagnostic agent.

This solution was pale yellow, transparent and had a pH of around 3.4.

EXAMPLE 10

Properties of $^{99m}$Tc-labeled, human serum albumin-combined GPPMTS:

In order to examine the labeling efficiency of the $^{99m}$Tc-labeled, human serum albumin-combined GPPMTS obtained in Example 8 or 9, its aqueous solution was subjected to thin layer chromatography using silica gel as a retention material and a mixture of n-butanol, acetic acid and water (4:1:1) as a developing solvent, and scanning was carried out by the use of a radiochromato-scanner. The radioactivity was recorded as a single peak at the original point. Any peak due to a radioactive impurity such as free pertechnetate ion (Rf=0.8) was not recognized.

Then, the $^{99m}$Tc-labeled, human serum albumin-combined GPPMTS obtained in Example 8 or 9 was subjected to electrophoresis (500 V; 15 minutes) using a Veronal buffer (pH, 8.6; ion intensity, 0.07) as a developing solvent and a cellulose acetate membrane (2 cm wide) as an electrophoretic membrane, and scanning was effected by the use of a radiochromato-scanner. The radioactivity was recognized as a single peak at the locus of 1.8 cm distant from the original line towards the positive side. This locus was the same as that of the coloring band of human serum albumin with Ponceau 3R.

From the above results, it may be said that the $^{99m}$Tc-labeled, human serum albumin-combined GPPMTS obtained in Example 8 or 9 has a labeling efficiency of nearly 100%, and its electric charge is substantially the same as that of human serum albumin.

EXAMPLE 11

Behaviors of $^{99m}$Tc-labeled, human serum albumin-combined GPPMTS in mice:

The $^{99m}$Tc-labeled, human serum albumin-combined GPPMTS obtained in Example 8 or 9 (0.05 ml) was administered intravenously to each of female mice of DDY strain at the tail vein, and the variations of the blood level and the organ distribution with the lapse of time were recorded. The results are shown in Tables 1 and 2.

Further, the variations of the blood level and the radioactivity concentration in stomach with the lapse of time were examined on the $^{99m}$Tc-labeled, human serum albumin-combined GPPMTS obtained in Example 8 (Sample A) and the commercial products of $^{99m}$Tc-labeled, human serum albumin (Sample B) and of $^{131}$I-labeled, human serum albumin (Sample C) for comparison. The results are shown in FIG. 1 of the accompanying drawing, wherein the time after administration (minutes) and the distribution of radioactivity per unit weight (%/gram) are indicated respectively on the abscissa and the ordinate, and the lines have the following meanings:

○———○ : Blood level in case of Sample A (%/g)
△———△ : Blood level in case of Sample B (%/g)
□———□ : Blood level in case of Sample C (%/g)
●———● : Radioactivity concentration in stomach in case of Sample A (%/g)
▲———▲ : Radioactivity concentration in stomach in case of Sample B (%/g)
■———■ : Radioactivity concentration in stomach in case of Sample C (%/g)

TABLE 1

(using the radioactive diagnostic agent obtained in Example 8)

| Organs | Time after administration (min) | | |
|---|---|---|---|
| | 10 | 30 | 60 |
| Blood | 33.89 | 26.64 | 25.36 |
| Liver | 7.80 | 8.16 | 9.30 |
| Kidneys | 10.17 | 9.45 | 10.02 |
| Intestine | 1.24 | 1.85 | 2.82 |
| Stomach | 0.83 | 1.34 | 2.40 |
| Spleen | 4.10 | 4.18 | 4.81 |
| Lung | 10.44 | 9.42 | 7.54 |
| Heart | 6.01 | 6.09 | 5.84 |

TABLE 2

(using the radioactive diagnostic agent obtained in Example 9)

| Organs | Time after administration (min) | | |
|---|---|---|---|
| | 10 | 30 | 60 |
| Blood | 29.03 | 23.54 | 19.87 |
| Liver | 8.75 | 9.79 | 9.47 |
| Kidneys | 9.85 | 11.03 | 11.36 |
| Intestine | 1.13 | 1.98 | 2.61 |
| Stomach | 1.23 | 1.85 | 2.42 |
| Spleen | 3.55 | 3.72 | 3.15 |
| Lung | 8.89 | 9.44 | 6.95 |
| Heart | 4.94 | 4.27 | 4.24 |

Note:
In Tables 1 and 2, each value is an average in 5 animals. The body weight was standardized to 190 grams. Organs contained blood.

From the above results, it is understood that the $^{99m}$Tc-labeled, human serum albumin-combined GPPMTS can maintain a remarkably high blood level for a long period of time in comparison with conventional $^{99m}$Tc-labeled, human serum albumin. It is also understood that the $^{99m}$Tc-labeled, human serum albumin-combined GPPMTS shows a nearly equal blood level to that of conventional $^{131}$I-labeled, human serum albumin with a long retention in blood. It is further understood that the $^{99m}$Tc-labeled, human serum albumin-combined GPPMTS is quite stable in a living body and gives a relatively low radioactivity at various organs in comparison with the blood level. Thus, the $^{99m}$Tc-labeled, human serum albumin-combined GPPMTS is quite suitable for the use in nuclear medical diagnosis aiming at recording, dynamic study and quantitative measurement of the blood circulation system.

Example 12

Stability of human serum albumin-combined GPPMTS:

The human serum albumin-combined GPPMTS obtained in Example 5 was stored in a refrigerator at 4° to 8° C. for 30 days and then treated with $^{99m}$Tc according to the procedure as in Example 8 to give an aqueous solution containing the $^{99m}$Tc-labeled, human serum albumin-combined GPPMTS. With this solution, thin layer chromatography and electrophoresis were carried out according to the procedure as in Example 10 and also behaviors in mice were examined according to the procedure as in Example 11. The results were substantially the same as in Examples 10 and 11. Thus, it may be said that no material change is produced in the human serum albumin-combined GPPMTS by the storage for 30 days.

EXAMPLE 13

Stability of human serum albumin-combined GPPMTS:

The human serum albumin-combined BETS (lyophilized powder) obtained in Example 6 was stored in a refrigerator at 4° to 8° C. for 30 days and then treated with $^{99m}$Tc according to the procedure as in Example 9 to give an aqueous solution containing the $^{99m}$Tc-labeled, human serum albumin-combined GPPMTS. With this solution, thin layer chromatography and electrophoresis were carried out according to the procedure as in Example 10 and also behaviors in mice were examined according to the procedure as in Example 11. The results were substantially the same as in Examples 10 and 11. Thus, it may be said that no material change is produced in the human serum albumin-combined GPPMTS by the storage for 30 days.

EXAMPLE 14

Stability of $^{99m}$Tc-labeled, human serum albumin-combined GPPMTS:

An aqueous solution containing the $^{99m}$Tc-labeled, human serum albumin-combined GPPMTS obtained in Example 9 was stored at room temperature (24°–27° C.) for 36 hours. With this solution, thin layer chromatography and electrophoresis were carried out according to the procedure as in Example 10 and also behaviors in rats were examined according to the procedure as in Example 11. The results were substantially the same as in Examples 10 and 11. Thus, it may be said that no material change is produced in the $^{99m}$Tc-labeled, human serum albumin-combined GPPMTS by the storage of 36 hours.

EXAMPLE 15

Toxicity of the non-radioactive carriers:

The non-radioactive carrier obtained in Example 6 was administered intravenously to groups of male and female rats of SD strain, each group consisting of 10 animals, at a dose of 1 ml per 100 grams of the bodyweight (corresponding to 400 times the expected dose to human beings) and also to groups of male and female mice of ICR strain, each group consisting of 10 animals, at a dose of 0.5 ml per 10 grams of the bodyweight (corresponding to 2000 times the expected dose to human beings). As the control, the same volume of a physiological saline solution as above was intravenously administered to the separate groups of the same animals as above.

The animals were fertilized for 10 days, and the variation in bodyweight during that period was recorded. No significant difference was recognized between the medicated groups and the control groups.

After 10 days from the administration, all the animals were sacrificed and subjected to observation of the abnormality in various organs. But, no abnormality was seen in any of the animals.

From the above results, it may be said that the toxicity of the non-radioactive carrier of the invention is extremely low.

EXAMPLE 16

Toxicity of the radioactive diagnostic agent:

The $^{99m}$Tc-labeled, human serum albumin-combined GPPMTS obtained in Example 9 was subjected to attenuation of the radioactivity to an appropriate extent, and the resultant product was subjected to test for toxicity in the same manner as in Example 15. No significant difference was recognized between the medicated groups and the control groups. In all the animals sacrificed after 10 days from the administration, no abnormality was observed in their organs. Thus, it may be said that the radioactive diagnostic agent of the invention does not produce any material toxicity in tested animals even when administered in such a large dose as corresponding to 300 to 1500 times the expected dose to human beings.

What is claimed is:

1. A compound of the formula:

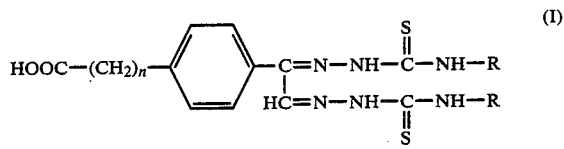

wherein R is a hydrogen atom or a $C_1$–$C_3$ alkyl group and n is an integer of 0 to 4.

2. The compound according to claim 1, wherein R is methyl.

3. The compound according to claim 2, wherein n is 1.

4. The compound according to claim 2, wherein n is 2.

5. The compound according to claim 2, wherein n is 3.

6. The compound according to claim 2, wherein n is 4.

7. A physiologically active substance-combined compound comprising the compound according to claim 1 and a physiologically active substance bound therewith by a chemical bond.

8. The physiologically active substance-combined compound according to claim 7, wherein the chemical bond is a carbonamide linkage.

9. The physiologically active substance-combined compound according to claim 7, wherein the physiologically active substance is human serum albumin.

10. A radioactive metallic element-labeled, physiologically active substance-combined compound comprising the compound according to claim 1, a physiologically active substance bound therewith by a chemical bond and a radioactive metallic element bound with said compound through a chelating bond.

11. The radioactive metallic element-labeled, physiologically active substance-combined compound according to claim 10, wherein the radioactive metallic element is $^{99m}$Tc.

12. A process for preparing the physiologically active substance-combined compound according to claim 7, which comprises reacting the compound according to claim 1 with a physiologically active substance.

13. The process according to claim 12, wherein the physiologically active substance has an amino group, and the reaction proceeds between the carboxyl group in the compound according to claim 1 and the amino group in the physiologically active substance to form a carbonamide linkage.

14. A process for preparing the radioactive metallic element-labeled, physiologically active substance-combined compound according to claim 10, which comprises contacting the physiologically active substance-combined compound according to claim 7 with a radioactive metallic element to combine them through a chelating bond.

15. The process according to claim 14, wherein the contact is carried out in an aqueous medium.

16. The process according to claim 15, wherein the contact is carried out in the presence of a reducing agent.

17. A non-radioactive carrier comprising the physiologically active substance-combined compound according to claim 7.

18. The non-radioactive carrier according to claim 17, which is in the form of solution.

19. The non-radioactive carrier according to claim 17, which is in the form of lyophilized powder.

20. A radioactive diagnostic agent comprising the radioactive metallic element-labeled, physiologically active substance-combined compound according to claim 10.

* * * * *